US012661317B2

(12) United States Patent (10) Patent No.: US 12,661,317 B2
Quintana Hau et al. (45) Date of Patent: Jun. 23, 2026

(54) OPHTHALMIC PHARMACEUTICAL COMPOSITION, PREPARATION METHODS AND USES OF THE SAME

(71) Applicant: SOPHIA HOLDINGS, S.A. DE C.V., Guadalajara (MX)

(72) Inventors: Juan de Dios Quintana Hau, Guadalajara (MX); Luciano Pesqueda Pinedo, Guadalajara (MX); Humberto Figueroa Ponce, Guadalajara (MX); Addy Linan Segura, Guadalajara (MX)

(73) Assignee: Sophia Holdings, S.A. DE C.V., Guadalajara (MX)

( * ) Notice: Subject to any disclaimer, the term of this patent is extended or adjusted under 35 U.S.C. 154(b) by 1144 days.

(21) Appl. No.: 17/636,138

(22) PCT Filed: Sep. 4, 2020

(86) PCT No.: PCT/MX2020/050031
§ 371 (c)(1),
(2) Date: Jul. 26, 2022

(87) PCT Pub. No.: WO2021/045606
PCT Pub. Date: Mar. 11, 2021

(65) Prior Publication Data
US 2022/0354788 A1 Nov. 10, 2022

(30) Foreign Application Priority Data
Sep. 6, 2019 (MX) .................... MX/a/2019/010618

(51) Int. Cl.
| A61K 9/107 | (2006.01) |
| A61J 1/14 | (2023.01) |
| A61K 9/00 | (2006.01) |
| A61K 31/047 | (2006.01) |
| A61K 47/24 | (2006.01) |
| A61K 47/36 | (2006.01) |
| A61K 47/44 | (2017.01) |
| A61P 27/04 | (2006.01) |

(52) U.S. Cl.
CPC ........... *A61K 9/1075* (2013.01); *A61J 1/1468* (2015.05); *A61K 9/0048* (2013.01); *A61K 31/047* (2013.01); *A61K 47/24* (2013.01); *A61K 47/36* (2013.01); *A61K 47/44* (2013.01); *A61P 27/04* (2018.01)

(58) Field of Classification Search
None
See application file for complete search history.

(56) References Cited

U.S. PATENT DOCUMENTS

| 5,166,331 | A | * | 11/1992 | della Valle | ........... | A61K 9/0019 |
| | | | | | | 514/420 |
| 6,132,751 | A | | 10/2000 | Suzuki et al. | | |
| 2005/0196370 | A1 | * | 9/2005 | Yu | ......................... | A61L 12/143 |
| | | | | | | 424/70.13 |
| 2011/0173928 | A1 | * | 7/2011 | Fetz | ........................ | A61L 2/206 |
| | | | | | | 53/426 |
| 2016/0101050 | A1 | | 4/2016 | Lee et al. | | |
| 2017/0119811 | A1 | * | 5/2017 | Klein | ..................... | A61K 9/127 |
| 2019/0255096 | A1 | | 8/2019 | Ketelson et al. | | |

FOREIGN PATENT DOCUMENTS

| CN | 101391111 A | 3/2009 |
| DE | 102014203152 A1 | 8/2015 |
| EP | 2664330 A1 | 11/2013 |
| WO | 2011138228 A1 | 11/2011 |
| WO | 2018071619 A1 | 4/2018 |

OTHER PUBLICATIONS

Lilia Petit Ben Saidane; How to deliver preservative-free eye drops in a multidose system with a safer alternative to filters?. Invest. Ophthalmol. Vis. Sci. 2017;58(8):4460. (Year: 2017).*
Marta Vicario De La Torre, et al., "Novel Nano-Liposome Formulation for Dry Eyes with Components Similar to the Preocular Tear Film", Polymers 10(4), 425 (2018).
Anonymous "Systane® Balance Gotas Oftalmicas Lubricantes 10 ML", farmaciavence, (Mar. 5, 2019), URL: http://www.farmaciavence.com//vistas/producto/systane-balance-gotas-oftalmicas-lubricantes-10-ml.aspx.
Anonymous "Systane® Complete Lubricant Eye Drops Ingredients and Usage", Systane, (2019), URL: https://systane.myalcon.com/eye-care/systane/products/systane-complete/ingredients.
PMFarma "Alcon presenta en España Systane Complete" PMFarma, 2019, URL: http://www.pmfarma.es/noticias/26861-alcon-presenta-en-espana-systane-complete-la-lagrima-artificial-de-ultima-generacion-para-el-ojo-seco.html.
International Search Report and Written Opinion corresponding to International Patent Application No. PCT/MX2020/050031 mailed Dec. 22, 2020, 13 pages.

* cited by examiner

*Primary Examiner* — Ali Soroush
*Assistant Examiner* — Afua Bamfoaa Boateng
(74) *Attorney, Agent, or Firm* — Myers Bigel, P.A.

(57) ABSTRACT

The present invention relates to ophthalmic compositions in the form of oil-in-water (O/W) nano-emulsions, and which mainly comprise propylene glycol and sodium hyaluronate. The invention also relates to preparation methods and uses of the artificial tear compositions.

20 Claims, 8 Drawing Sheets

Carbon mesh

Oil particles

Frozen sample (ice)

Carbon mesh

Frozen sample (ice)

Castor oil particles

Size (d.nm)

Size (d.nm)

Apparent Z potential (mV)

Apparent Z potential (mV)

Movility (μmcm/Vs)

Movility (μmcm/Vs)

OPHTHALMIC PHARMACEUTICAL COMPOSITION, PREPARATION METHODS AND USES OF THE SAME

FIELD OF INVENTION

This invention relates to ophthalmic pharmaceutical compositions, specifically to ophthalmic compositions in the form of emulsions of the oil-in-water (O/W) type; more specifically the present invention is in the form of nano-emulsions comprising propylene glycol. The invention is also directed to ophthalmic compositions that do not generate a high viscosity due to the emulsification process and do not contain preservatives within their formulation. Additionally, the present invention is also directed to the preparation processes of the same and its use as a composition that, among other benefits, provides lubrication to the ocular surface, stabilizing the tear film, while avoiding the evaporation of said film that is formed during its administration. Likewise, the present invention is directed to a system that allows containing ophthalmic compositions free of preservatives, as well as for their administration.

DESCRIPTION OF THE RELATED ART

Different compositions of artificial tears that allow the treatment of anomalies in the tear layer of the eye are known in the state of the art. Such conditions are commonly caused by the failure of the eye to produce either a suitable amount or maintain a proper balance of the lacrimal components of the mucosa.

In general terms, a natural tear is made up of a lipid phase (triglycerides, fatty acids, cholesterol, phospholipids and glycolipids); an aqueous serous phase (proteins, electrolytes (sodium, magnesium, calcium, chlorine, bicarbonate ions)); and a mucin phase (proteins, hydrocarbons and enzymes).

In contrast, an artificial tear is essentially composed of a lipid phase and an aqueous phase (lubricant, electrolytes, glycerin, polymers).

In this regard, current artificial tear compositions designed to reduce or relieve moderate to severe dry eye contain polymers that act to mimic the mucosal, aqueous, and/or lipid layers of the tear film to maintain film stability and decrease tear film stability. rapid evaporation (Horn et al, 2017).

However, the ocular bioavailability of topically applied drugs is very limited due to the efficient protection mechanisms that guarantee the correct functioning of the eye. These barriers are difficult to overcome by instilled drugs. Another problem to be considered is to achieve an optimum concentration of the drug at the site of action (Souto et al. 2010).

The strategies for improving the efficacy of topical treatments and overcoming ocular barriers remain an important objective for the delivery of ocular drugs. In general, most successful delivery systems are present on the ocular surface for an extended period, and these systems generally improve the bioavailability of the drug in the anterior chamber (Rawas qalaei And Williams, 2012).

During the last decades, several drug delivery systems, such as liposomes, nano-emulsions, microemulsions, nanoparticles, and dendrimers, have become novel strategies for improving the bioavailability of ocular drugs (Souto Et al. 2010).

The nanoparticle technologies generally have several benefits, for example, the solubilization of hydrophobic and poorly soluble drugs; improving bioavailability and pharmacokinetic properties; coupled to the protection of drugs against physical, chemical, and biological degradation. Moreover, the size of the sub-micron of these systems allows for efficient transport and the crossing of biological barriers that protect the eye, thereby allowing proper administration of medicaments to the target site.

Referring the above cited, the nanometric emulsions, also referred to in the literature as miniemulsions, ultrafine emulsions and sub-micron emulsions, are emulsions with nanometric size droplets (less than 100 nm).

Despite the similar appearance between both types of colloidal dispersions, it is important to note that, unlike microemulsions, which are thermodynamically stable (i.e., spontaneously formed) systems, nano-emulsions are thermodynamically unstable, requiring energy to their formation.

The source of the energy required may be external (methods of dispersive or high energy) or internal (condensing or low energy methods). High energy emulsion methods utilize mechanical devices to generate strong disruptive forces that break the oil and water phases to produce small droplets. The most used devices for producing nano-emulsions are stator-rotor systems, high-pressure and ultrasound systems.

Other high-energy emulsification methods, which have been developed intensively in recent years, are microfluidic methods, which provide practically monodisperse droplets and are characterized by relatively low energy consumption, and membrane methods.

In this regard, for example, the international application No. WO/2018/071619 discloses artificial tear and contact lens storage compositions comprising one or more non-ionic surfactants, as well as thickening agents, a polyol, and an electrolyte, such as sodium chloride. In said document is disclosing a "moisture-trapping" or Moisture-Lock effect which lies in a purely mechanical action derived from the interaction that exists during the instillation of a drop with a high degree of viscosity (300-400 cps), nevertheless, the use of very viscous drops eventually causes blurred vision in the user.

On the other hand, US Pat. Appl. Nr. 2016/0101050 relates to an ophthalmic nano-emulsion which allows to increase the solubility of an active agent such as cyclosporin, while achieving improved stability of the entire composition. Although, in comparison to other compositions, the particle size distribution is not substantially homogeneous.

In turn, the CN patent application Nr. 101391111 discloses solutions for the care of contact lenses and drops to moisturize the eyes, using essentially polyoxylated castor oil (modified to be water soluble) and bactericidal agents.

In view of the above, there is a need for artificial tear compositions that promote lubrication of the ocular surface, avoiding any drawbacks mentioned above. Also, there is a need for compositions that maintain the integrity and efficacy of contact lenses intact. Moreover, there is a need for a preservative free artificial tear composition.

SUMMARY OF THE INVENTION

It is therefore an object of the present invention to provide ophthalmic compositions in the form of nano-emulsions that comprise, in one of the modalities of the present invention, an organic compound formed by a diol, a stable polymer, preferably a polymer of the glycosaminoglycan type, fatty acids or phospholipids and other pharmaceutically acceptable excipients.

In other preferred embodiment of the present invention, the organic compound comprising a diol is propylene glycol.

Moreover, in another embodiment of the present invention, the glycosaminoglycan type polymer is preferably sodium hyaluronate.

Additionally, in other preferred embodiment, phospholipids comprise 1,2-dimyristoyl-sn-glycero-3-phosphocholine (DMPC) and castor oil.

It is a further object of the present invention to provide artificial tear compositions that do not further cause damage to the contact lenses and permit the relief of non-bacterial conjunctivitis.

In another objective of the present invention, ophthalmic compositions are provided wherein the use of sodium hyaluronate does not generate a high viscosity.

In a preferred embodiment of the present invention, sodium hyaluronate is subjected to an emulsification process by high impact, which results in the fragmentation of this polymer into monomers dispersed in the formulation, thus allowing the active ingredients to migrate more effectively to the corneal epithelium and assist it in their recovery.

In a further objective of the present invention, ophthalmic compositions are provided, which provide lubrication to the ocular surface by stabilizing the tear film while avoiding the evaporation of said film that formed during its administration.

In another objective of the present invention, processes for the preparation of the ophthalmic compositions are provided.

In another objective, a system which allows for containing the ophthalmic compositions free of preservatives is provided, as well as for the administration thereof.

DETAILED DESCRIPTION OF THE INVENTION

Figure 1A:
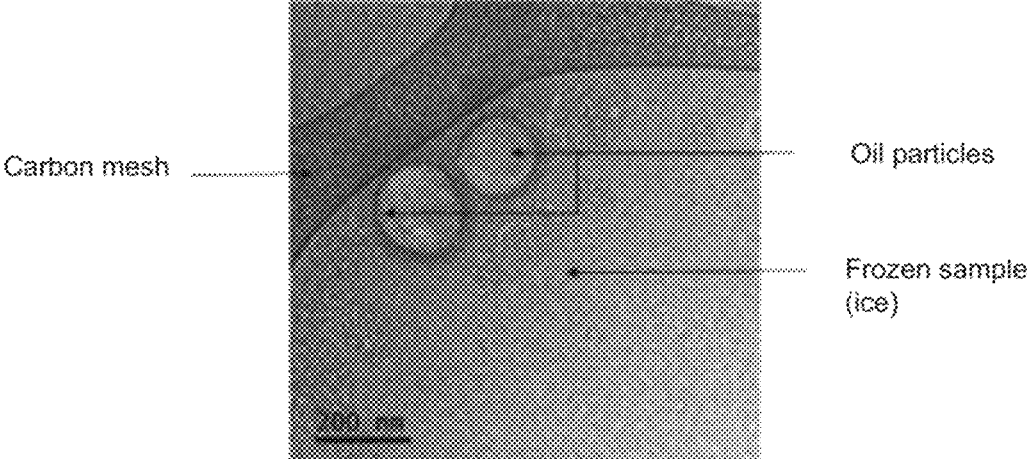
FIGS. 1A and 1B show comparative electron microscopy images between the Systane Balance® commercial product (1A) and the ophthalmic composition of the present invention (1B).

The aspects of the present invention will now be described in more detail using further reference to the accompanying figures, wherein some, but not all, of the advantages of the present invention are shown. Indeed, various embodiments of the invention may be expressed in many ways and should not be interpreted as being limited to the embodiments described herein; rather, these exemplary embodiments are provided so that this invention is exhaustive and complete, and will fully convey the scope of the invention to those skilled in the art. For example, unless otherwise noted, something described as first, second, or the like should not be construed as a particular order. As used in the description and the claims, the singular forms "a", "an", "the", include plural referents unless the context clearly indicates otherwise.

The aspects of the present invention refer to ophthalmic compositions, preferably in the form of oil-in-water (O/W) nano-emulsions, which are clearly administered via ophthalmic.

As used herein, the term "compositions" is intended to encompass products comprising the specified compounds in the specified amounts, as well as any products that result, directly or indirectly, from a combination of the specified compounds in the specified amounts.

Thus, in one embodiment of the present invention, the ophthalmic compositions are substantially treated with isotonic, sterile and homogeneous nano-emulsions containing polyols such as propylene glycol, polyethylene glycol 300, Sorbitol.

In a preferred embodiment, the present composition comprises propylene glycol at a concentration, preferably between 0.1 to 0.6%.

In another embodiment of the present invention, the ophthalmic compositions may further contain a stable polymer, of the glycosaminoglycan type, such as guar gum, Gellan gum, hydroxypropyl methylcellulose, sodium hyaluronate, hydroxyethyl cellulose, methylcellulose, polyvinylpyrrolidone, polyvinyl alcohol, fatty acids and other pharmaceutically acceptable excipients.

In preferred embodiments, the stable polymer is sodium hyaluronate. In preferred embodiments, the fatty acids or phospholipids comprise DPPC (1,2-dipalmitol-sn-glycero-3-phosphocholine), DSPC (1,2-distearol-sn-glycero-3-phosphocholine, DOPC (1,2-Dioleol-sn-glycero-3-phosphocholine, DEPC (1,2-dierucil-sn-glycero-3-phosphocholine), but not limited, the fatty acid used to be 1,2-dimyristoyl-sn-glycero-3-phosphatidylcholine (DMPC) and castor oil.

In the context of the present invention the propylene glycol is an organic compound (an alcohol, more precisely a diol) colorless and tasteless and odorless that promotes lubrication at the ocular surface level by stabilizing the tear film and decreases the evaporation of the tear film.

The DMPC compound is a phospholipid (fatty acid) which is presented as an amphiphilic molecule, which is a structural part of the lipid bilayer of the cell membrane.

The castor oil acts as a co-solvent agent, providing the incorporation into the nano-emulsion of the surfactant, also integrated into the system (or emulsion) the compounds of the lipid nature present in the formulation, for example, to the fatty acids. Likewise, this component constitutes the oil phase of the present nano-emulsion oil in water (O/W).

In a more preferred embodiment of the present invention, the ophthalmic compositions comprise about:

Propylene glycol in an amount of 0.1 to 0.6%
Boric acid in an amount of 0.01 to 0.1%
Sodium borate decahydrate from 0.01 to 0.5%
Dimyristoyl phosphatidyl choline (DMPC) from 0.001 to 0.01%
Edetate disodium dihydrate from 0.01 to 0.1%
Sodium hyaluronate of 0.1 to 0.5%
Castor oil of 1.0 to 5.0%
Polysorbate 80 from 0.2 to 4.0%
Glycerin from 0.5 to 2.2%
Grade water for preparation of cbp injectable.

In the context of the present invention, the mixture of these components is subjected to homogenization by a physical method (high energy emulsion) to obtain the emulsion.

In another aspect of the present invention, the emulsions O/W have as one of its main properties, related to the stability and maintenance of the physicochemical characteristics, the particle size of the oil dispersed in the medium. According to techniques known to those skilled in the art, the most used technique for determining the above is the dynamic dispersion of the light, wherein a correlation of the particle size is established with respect to its movement.

Thus, in a preferred embodiment, in the present invention, the micelle formed by fatty acids or phospholipids has a particle size distribution ranging from about 30 nm to about 260 nm; more preferably a particle size distribution ranging from about 32 nm to about 255 nm. In a more preferred embodiment, the composition of the present invention has a particle size distribution of approximately 82.5 nm to approximately 92.5 nm.

In another aspect of the present invention, the composition in addition to functioning as an artificial tear, the inventors have found that the formulation achieves a completely unexpected first technical effect, that is, the compositions of the present invention provide lubrication to the ocular surface stabilizing the tear film and at the same time prevent the evaporation of said film. Also preventing any effect of blurred vision. This has been achieved by the migration of the components, as well as the particles or micelles made up of castor oil and DMPC that are integrated into the lipophilic layer of the natural tear.

The inventors of the present invention have also surprisingly found that in ophthalmic compositions, by subjecting sodium hyaluronate to a high-impact emulsification process, the fragmentation of this polymer into monomers dispersed in the formula is obtained, thus allowing the active ingredients migrate more effectively to the corneal epithelium and thus help in its recovery.

In this regard, the sodium salt of hyaluronic acid is incorporated into the emulsion to give body or viscous consistency, due to its polymeric structure which is made up of repeated disaccharide units of N-acetylglucosamine and D-glucuronic acid, linked by glycosidic bonds '1-'4.

During the manufacturing process of the compositions of the present invention, the long chains of sodium hyaluronate present are fragmented into small chains, by the action of shear and pressure generated during the three-cycle mechanical emulsification process in a pressure range of 10,000 psi (68947591 Pa) to 30,000 psi (206842773 Pa).

In another aspect of the present invention, a process for the manufacture of the ophthalmic compositions is provided. The development of the manufacturing process is carried out considering that the pharmaceutical form is an emulsion, also considering the characteristics of the components of the formula and its route of administration of the product (ophthalmic). The process seeks to obtain a stable homogeneous emulsion.

It should be noted that, in view of the preferred route of administration, a sterile product is required, according to the characteristics of the developed formula and the type of primary packaging, it is possible to apply terminal sterilization to the product. Therefore, a sterilization of the product is included by means of filtration, providing this filtered product into the sterile container closure system, in a sterile environment.

In a preferred embodiment, the formulation process is carried out in a stainless-steel tank using a stainless-steel propeller for agitation.

More preferably, the process described in the present application essentially consists of two stages in its formulation.

In the first stage of formulation, a tank is identified wherein the preparation is carried out, starting with the addition of between 60 and 65% of grade water for the manufacture of injectables to the tank with a temperature in the range of 20 to 30° C. and constant agitation is applied inside the tank, wherein the following components are added, maintaining a constant agitation and temperature range: Polysorbate 80, Dimiristil phosphatidyl choline (DMPC), Boric Acid, Sodium Borate decahydrate, Disodium Edetate dihydrate, Glycerin, Propylene Glycol, Sodium Hyaluronate, and finally Castor Oil, this last component being the oily phase of the system or emulsion (O/W).

At this point, this mixture of oily-aqueous preparation is added the grade water for the manufacture of injectables necessary to reach the predetermined capacity or volume, undergoing homogenization prior to the emulsification of this mixture.

In the second stage, this mixture of oily-aqueous preparations is subjected to the mechanical emulsification process. This emulsification must be carried out at a controlled pressure and temperature.

In a preferred embodiment, the addition for the formulation process, as well as the temperature conditions, can be the following:

| Component | Required Temperature |
|---|---|
| Grade water for the manufacture of injectables (60 to 65% of the volume necessary for manufacturing) | 20 a 35° C. |
| Polysorbate 80 | 20 a 35° C. |
| 1,2-Dimyristoyl-SN-glycero-3-phosphocholine (DMPC) | 20 a 35° C. |
| Boric acid | 20 a 35° C. |
| Sodium borate decahydrate | 20 a 35° C. |
| Edetate Disodium Dihydrate | 20 a 35° C. |
| Glycerin | 20 a 35° C. |
| Propylene Glycol (Active Ingredient) | 20 a 35° C. |
| Sodium hyaluronate | 20 a 35° C. |
| Castor oil | 20 a 35° C. |
| The formulation is considered a mixture of oil phase in water phase. | |
| Afore with grade water for the manufacture of injectables and Homogenization | 20 a 35° C. |
| Mechanical emulsification of homogenized mixture oily phase-aqueous phase. | 10,000 psi (68947591 Pa) to 30,000 psi (206842773 Pa) 20 to 30° C. |

In accordance with the present invention, Castor Oil, in addition to serving as a co-solvent to incorporate 1,2-Dimyristoyl-SN-glycero-3-phosphocholine (DMPC or Dimyristil phosphatidyl choline) into the formulation, because this excipient is a fatty acid, it also represents in the formulation the oily phase (or internal phase) of the emulsion, representing 1.0% of the total concentration of the components present in the artificial tear compositions.

According to the process described in stages 10 to 12, this 1.0% of Castor Oil is incorporated into the formulation, forming a mixture of oily phase with the aqueous phase, which is subjected to a 60-minute homogenization process and finally to a mechanical emulsification process of three cycles at a pressure in a pressure range of 10,000 psi (68947591 Pa) to 30,000 psi (206842773 Pa), thereby obtaining a homogenization of both phases of the emulsion.

During the development of the formulation process, it is verified that the agitation speed is in a range of 78 rpm-840 rpm that generates a flow inside the tank when solubilizing the raw materials, it will not present turbulence, which generates the incorporation of air inside the emulsion, taking care for this same reason the speed of homogenization prior to the emulsification process through the equipment.

Finally, the sterilization stage is carried out by filtration using two sterilizing membranes, preferably Polyethylsulfone, with a pore size of 0.2 μm. The filters used are subjected to a membrane integrity test as a control.

In a preferred embodiment, the indicated compounds are included in their respective proportions, taking care that the number of revolutions of agitation is in a range of 78 rpm-840 rpm, the solubilization time and the temperature of the product:

| | |
|---|---|
| Polysorbate 80 | 0.75% |
| 1,2-dimyristoyl-SN-glycero-3-phosphocholine (DMPC) | 0.005% |
| Boric acid | 0.100% |
| Sodium borate 10 H$_2$O | 0.32% |
| Disodium edetate 2 H$_2$O | 0.020% |
| Glycerin | 1.660% |
| Propylene glycol | 0.600% |
| Sodium hyaluronate | 0.100% |
| Castor oil | 1.000% |

In another aspect of the present invention, a system is provided that allows the preservative-free artificial tear compositions to be contained and administered.

An aspect of the system includes artificial tear compositions to promote ocular surface lubrication. The system also includes low-density polyethylene containers with an assembled high-density polyethylene closure-device, which has a silicone valves system and low-density polyethylene; it is also compatible with a wide range of viscosities, easy to use and requires little force to operate the mechanism.

Figure 11:
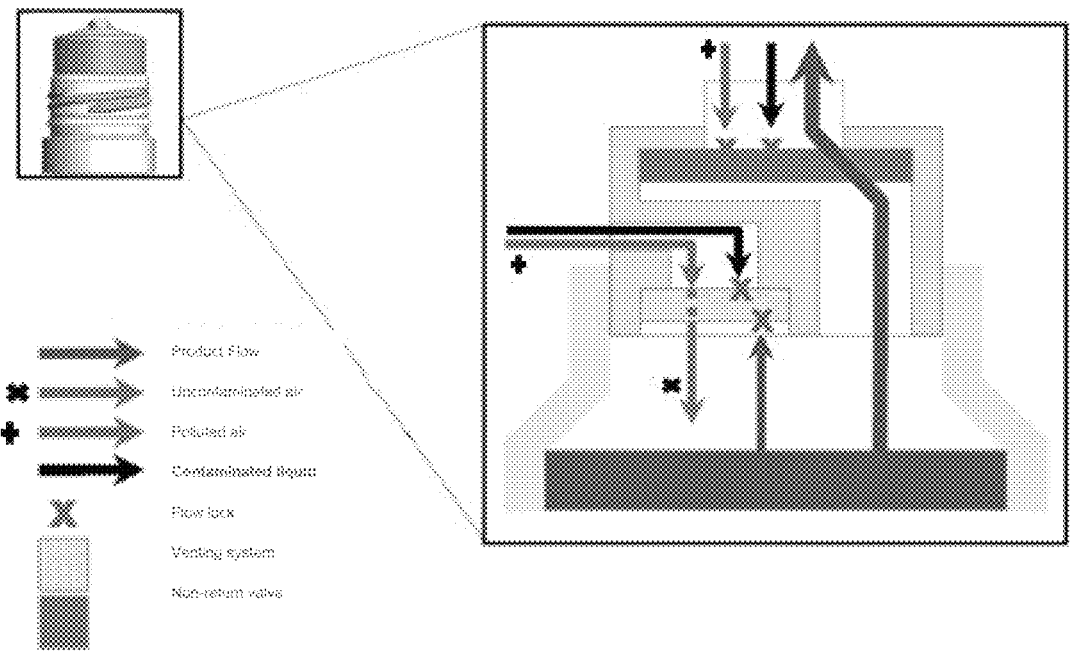
FIG. 11 shows a schematic of the mechanism of action or function of the container comprised in the system of the present invention.

The mechanism of action or function of this multidose container consists of dosing the product inside the bottle, preventing the entry of air and/or contaminated product from the outside by means of a non-return valve, compensating the internal air by means of a vent valve that filters the entry of contaminated air, and prevents the entry of contaminated liquids from the outside (FIG. 11).

Considering the damage caused to the corneas by the frequent use of preservatives, and the fact that some people may develop hypersensitivity to certain preservatives such as benzalkonium chloride (which is the most used preservative); the use of a system such as the one described in the present invention helps to minimize risks, mainly if they are long-term medications. In this regard, it has been shown that the frequent use of preservatives weakens the outer layer of the eye, leaving it very fragile.

In a related embodiment, the system provides all the components necessary for the administration of the artificial tear compositions in a safe and convenient manner.

In another embodiment of the system, the artificial tear compositions can be administered while preserving the sterile solution without the need for additives, such as antimicrobials and bacteriostatics.

In another related embodiment, the system allows the preservation and administration of the artificial tear compositions of the present invention, at an ideal pH of between 6.5 to 7.5 and an osmolality of 200 to 400 mOsmol/kg.

In another related embodiment, the system also comprises a buffer solution based on borates in a range not greater than 0.1%.

In another related embodiment, the system further comprises sodium hyaluronate in a corresponding ratio with the borate buffer, where greater stability of sodium hyaluronate is observed, for example:

| Sodium hyaluronate [BPM (%)] | Borate buffer system (%) |
|---|---|
| 0.10 | H$_3$BO$_3$ [0.1]-Na$_2$B$_4$O$_7$ [0.032] |

In another aspect of the present invention, both the system and the artificial tear compositions also allow maintaining contact lens integrity and commonly used parameters, such as overall diameter, thickness, UV light transmittance and diopters.

EXAMPLES

The invention is described below by means of specific examples, which only are intended to illustrate the features and advantages thereof, without this representing a limitation as to the scope and embodiments of the present invention.

Example 1

Artificial Tear Composition

| ACTIVE INGREDIENT | AMOUNT mg/mL | FUNCTION |
|---|---|---|
| Propylene glycol | 6.000 | Active Ingredient (Lubricant) |
| ADDITIVES | | |
| Boric acid | 1.000 | Buffer Agent |
| Sodium Borate Decahydrate | 0.320 | Buffer Agent |
| Dimyristoyl phosphatidyl choline (DMPC) | 0.050 | Fatty acid |
| disodium edetate dihydrate | 0.200 | Chelating Agent |
| Sodium hyaluronate | 1.000 | Dispersing Agent |
| Castor oil | 10.000 | Cosolvent Agent |
| Polysorbate 80 | 7.500 | Stabilizing Agent/Surfactant |
| Glycerin | 16.600 | Osmotic Agent |
| Grade water for preparation of injections c.b.p | 1.00 mL | Vehicle |

Example 2

The artificial tear compositions of the present invention were characterized for the microscopic morphology of micelles (oil particles); particle size distribution, conductivity, zeta potential, electrophoretic mobility, contact lens compatibility, and emulsion homogeneity.

a) Microscopic Characterization

The initial objective of the study was based on establishing the morphological differences and/or similarities between the composition of the present invention (referred to here as PRO-176) and the Systane Balance® commercial product. This study was carried out considering as a base as set forth in the article published in the journal Micron No. 43 of the year 2012 called "Electron microscopy of nano-emulsions: An essential tool for characterization and stability assessment" was taken as a basis. Klang et al., 2011. Wherein the use of a transmission electron microscope (electron transfer microscopy, MTE) is established, using the cryo-plung technique for the treatment of the sample. This study was conducted in conjunction with the National Polytechnic Institute of Mexico City.

Figure 1B:
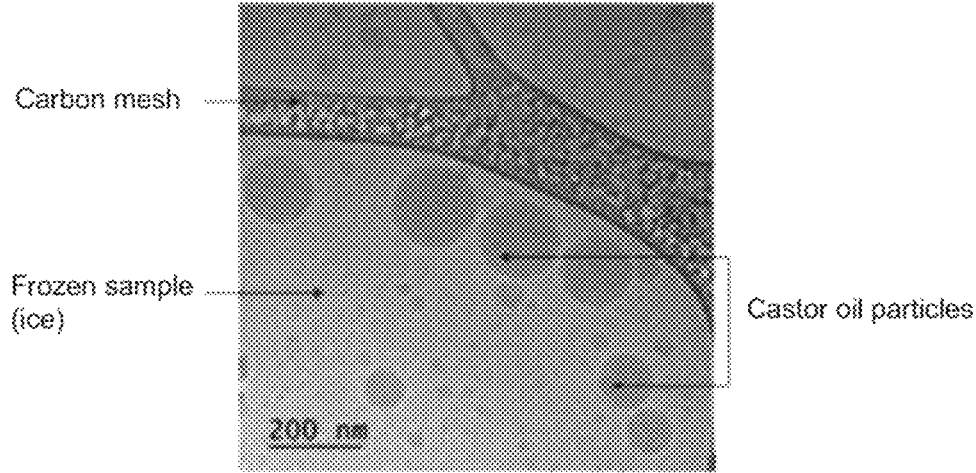

Based on the results obtained, a difference in the contrast of the layer around the castor oil particle can be observed in MTE images, both for PRO-176 (FIG. 1B) and for Systane Balance® (FIG. 1A). This is because, in the case of Systane Balance®, Dimyristil phosphatidyl glycerol (DMPG), has a lower electrical density, which is observed as a darker layer; in comparison with PRO-176, where Dimyristil phosphatidyl choline (DMPC), presenting a higher electrical density, shows a clearer layer.

b) Particle Size Distribution

The distribution of the particle size presented by PRO-176, and that of the Systane Balance® product, was characterized, using the equipment Zetasizer Model Nano ZSP (Red badge) Malvern brand.

Figure 2A:
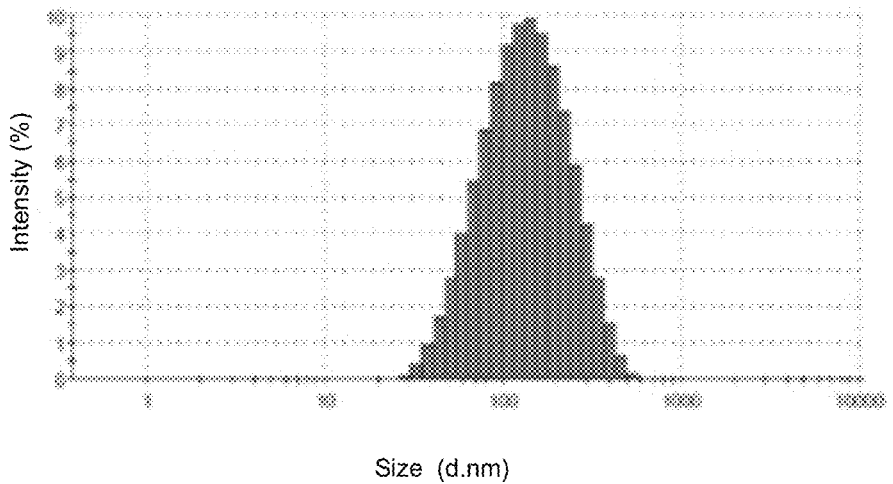
FIGS. 2A and 2B show comparative particle size distribution graphs showing the Systane Balance® commercial product (2A) and the ophthalmic composition of the present invention (2B).
Figure 2B:
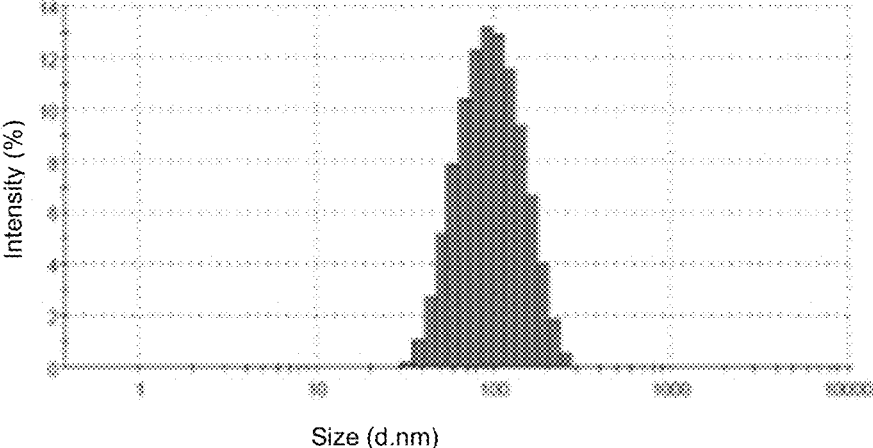

Referring to the particle size distribution, for the Systane Balance® (FIG. 2A), a population mean of 110.3 d was obtained. nm with a distribution that goes from 28.21 d. nm until 531.2 d. nm, within this range, a particle size of 141.8 d.nm is present in a higher percentage. In the case of PRO-176 (FIG. 2B), a population mean of 83.11 d. nm was obtained with a distribution that goes from 32.67 d. nm up to 255.0 d. nm, within this range a particle size of 91.28 d.nm is present in a higher percentage. Comparing these results for the two products, it can be concluded that the particle size distribution for PRO-176 is more homogeneous compared to Systane Balance®.

c) Zeta Potential

The purpose of this test was to characterize the contribution of electrostatic charge or zeta potential, which DMPC provides to the PRO-176 formula, and to verify if there is a difference and/or similarity with the contribution of charge or zeta potential presented by the present DMPG. in the formula of the reference product Systane Balance®. Using the equipment Zetasizer Model Nano ZSP (Red badge) Brand Malvern.

In this regard, since the viscosity of the sample is a necessary parameter to determine the zeta potential in the Zetasizer Model Nano ZSP (Red badge) Malvern equipment, it was necessary to make this determination according to the Brookfield DVT Extra Viscometer procedure. With these results, it was possible to edit the methods to determine the zeta potential, following the steps established in the procedure of the Zetasizer Model Nano ZSP (Red badge) Malvern brand equipment. The following table shows the results obtained:

| Sample | Batch | Volume of sample | Equipmet parameters | Viscosity |
|---|---|---|---|---|
| PRO-176 (Propylene glycol 0.6%) | 031740 | 16.0 mL. | Needle 00 (UL) Speed: | 2.20 mPas. |
| SYSTANE BALANCE ® | 263865F | 16.0 mL | 40 rpm. Time 2.0 min. | 2.02 mPas |

Figure 3A:
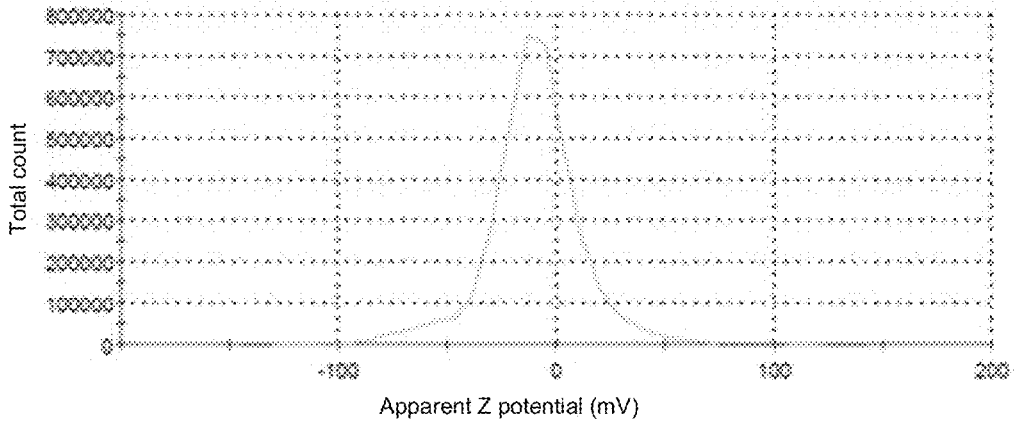
FIGS. 3A and 3B show comparative zeta potential graphs for the Systane Balance® commercial product (3A) and the ophthalmic composition of the present invention (3B).
Figure 3B:
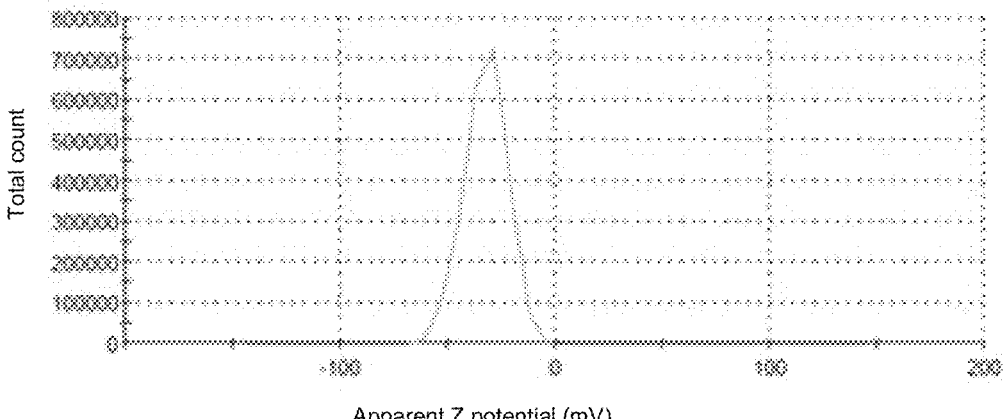

The Zeta potential result for the PRO-176 Lot 031740 (FIG. 3B) is −32.6 mV and for the Systane Balance® product (FIG. 3A) Lot 263865F, its result is −10.7 mV.

Considering that the Zeta potential refers to the stability of the nano-emulsion based on the interaction of charges present between the fat particles (liposome), and the surrounding medium (system); the nano-emulsion classification scale according to the value of zeta potential, it is considered that the values that are closer to 0 mV (isoelectric point) are less stable, and the values that are above +/−30 mV are more stable.

According to the results obtained, and considering the previous scale, it is possible to establish that the composition of PRO-176 (Zeta Potential=−32.6 mV), has greater stability with respect to the reference product Systane Balance® (Zeta Potential=−10.7 mV).

d) Electrophoretic Mobility

The purpose of this test was to determine the value of electrophoretic mobility provided by DMPC to the present composition. Similarly, the contribution of DMPG present in the formula of the Systane Balance® product was verified. Using the equipment Zetasizer Model Nano ZSP (Red badge) Brand Malvern. In this measurement, the conductivity data for both formulas are also acquired.

In this regards, electrophoretic mobility is the rate of migration of positively or negatively charged particles towards the oppositely charged electrode. Therefore, the electrophoretic mobility value is represented in units of velocity (μm cm/Vs).

Figure 4A:
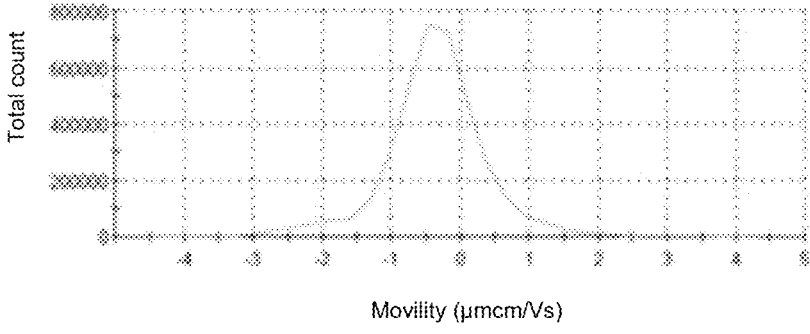
FIGS. 4A and 4B show comparative electrophoretic mobility graphs for the Systane Balance® commercial product (4A) and for the ophthalmic composition of the present invention (4B).
Figure 4B:
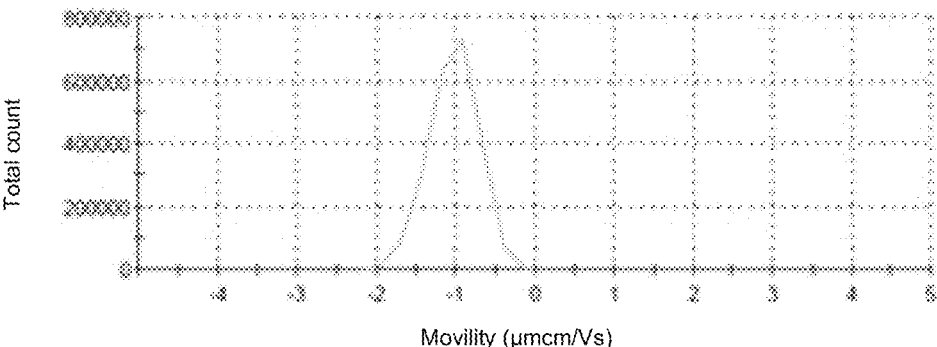

The electrophoretic mobility for the Systane Balance® product (FIG. 4A) is −0.3696 μm cm/Vs and the PRO-176 value (FIG. 4B) is −1.029 μm cm/Vs, both values are close to zero on the scale. negative, indicating that the two products have an anionic charge modifier. However, the conductivity present in the Systane Balance® product (2.47 mS/cm) is higher compared to that obtained in PRO-176 (0.379 mS/cm), this marks a benchmark in the ionic charge present in a formulation, being higher in Systane Balance®, due to the number of components and their quantity present in this formula.

In another study carried out for conductivity, the same equipment was used to characterize the present composition in comparison to the commercial product Systane Balance® and in terms of the fatty acid used in each formulation.

The conductivity meter is SEVEN Go Mettler Toledo. The implementation of the methodology consisted of steps known to those skilled in the art, two batches were used, one of each of the formulations (PRO-176 and Systane Balance®). The viscosity of the samples at a temperature of 25° C. was considered, using the refractive index and dielectric constant of water (1.33/78.50, respectively).

The results were the following:

| Sample | Batch | Conductivity with Malvern Zetasizer equipment (mS/cm) | Conductivity with the SEVEN Go Mettler Toledo equipment (µS/cm) |
|---|---|---|---|
| PRO-176 | 031740 | Reading 1: 0.388 mS/cm<br>Reading 2: 0.398 mS/cm<br>Reading 3: 0.402 mS/cm<br>Average: 0.396 mS/cm | 376 |
| Systane Balance ® | 263865F | Reading 1: 1.83 mS/cm<br>Reading 2: 2.32 mS/cm<br>Reading 3: 2.44 mS/cm<br>Average: 2.19 mS/cm | 2200 |

Because conductivity is a parameter inversely proportional to the resistivity of the medium in relation to the surrounding particles in it. High conductivity values reflect lower resistivity between charged oil particles; thus, causing the union between them, which leads to their coalescence, resulting in the separation between the oily and aqueous phases. Consequently, the lower the conductivity, the higher the stability of the product.

e) Compatibility with Contact Lenses

The use of contact lenses is related to eye irritation, due to the time they remain on the surface of the eye. For this reason, it is necessary for some users of this type of lens to maintain optimal lubrication in the eye, thus avoiding the mechanical effect caused by the friction produced by the lens on the ocular surface.

This test was conducted to evaluate the PRO-176 composition and Systane Balance® product, when used in conjunction with soft contact lenses.

In the test, two brands of contact lenses were evaluated, with two different diopters each. Physical changes were assessed in them when subjected to both formulations. This test was carried out in accordance with the ISO 11981: 2009 guide, evaluating the following parameters: total diameter, thickness, U.V. light transmission and diopter.

The results are shown in the following two tables, one for each brand of contact lens. They express wherein parameters damage was presented due to the use of each product. Damage to the contact lens is considered when presented in the analyzed parameter.

| | | Lente de contacto Tipo I | |
|---|---|---|---|
| Diopter of Lens | Test product | Parameter | There is damage/No damage |
| Diopter 1.0 | PRO-176 | Overall diameter | No damage |
| | | Thickness | No damage |
| | | UV Light Transmittance | No damage |
| | | Diopter | No damage |
| | Systane Balance ® | Overall diameter | No damage |
| | | Thickness | No damage |
| | | UV Light Transmittance | No damage |
| | | Diopter | No damage |
| Diopter 6.0 | PRO-176 | Overall diameter | No damage |
| | | Thickness | No damage |
| | | UV Light Transmittance | No damage |
| | | Diopter | No damage |
| | Systane Balance ® | Overall diameter | No damage |
| | | Thickness | No damage |
| | | UV Light Transmittance | No damage |
| | | Diopter | No damage |

It is seen from the above Tables that the Systane Balance® product affects the UV light transmittance, overall diameter and thickness of the contact lens.

| | | Lente de contacto Tipo IV | |
|---|---|---|---|
| Diopter of Lens | Control Solution/ Test product | Parameter | There is damage/No damage |
| Dioptria 1. 0 | PRO-176 | Overall diameter | No damage |
| | | Thickness | No damage |
| | | UV Light Transmittance | No damage |
| | | Diopter | No damage |
| | Systane Balance ® | Overall diameter | There is damage |
| | | Thickness | |
| | | UV Light Transmittance | No damage |
| | | Diopter | No damage |
| | | | No damage |
| Dioptria 6.0 | PRO-176 | Overall diameter | No damage |
| | | Thickness | No damage |
| | | UV Light Transmittance | No damage |
| | | Diopter | No damage |
| | Systane Balance ® | Overall diameter | No damage |
| | | Thickness | No damage |
| | | UV Light Transmittance | No damage |
| | | Diopter | No damage |

In the Table above, it is observed for the 1.0 diopter Type IV Lens, the Systane Balance® product affects the total diameter in this contact lens.

In conclusion, for the PRO-176 composition, there was no change in both types of contact lenses in the two diopters analyzed (1.0 and 6.0), compared to the changes and alterations that these lenses suffered when exposed to the product Systane Balance®.

f) Homogeneity of the Emulsion

According to established procedures on the label of the Systane Balance® commercial product, it needs to be shaken "well" before instillation.

In the case of PRO-176, the use of this legend is not necessary since, in relation to the "Particle Size Distribution" study, the particle size range is 32.67 d. nm up to 255.0 d. nm, which is lower compared to the commercial product (28.21 d.nm to 531.2 d.nm).

Figures 5A, 5B:
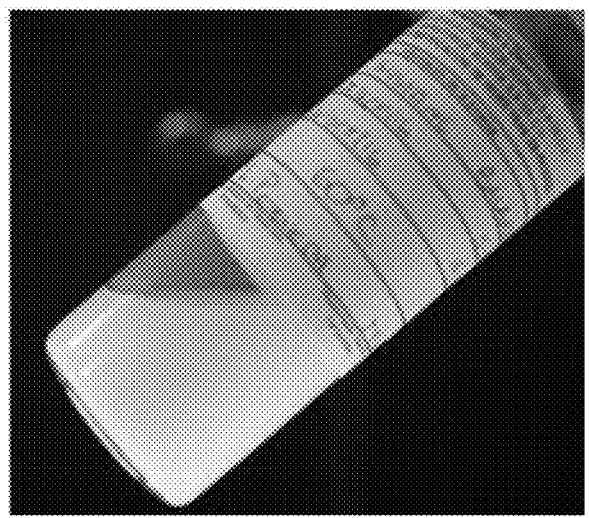
FIGS. 5A and 5B show comparative regarding homogeneity tests graphs for the Systane Balance® commercial product (FIG. 5A) and for the ophthalmic composition of the present invention (5B).

This difference can be seen macroscopically by subjecting the commercial product (FIG. 5A) to 60° C. for 21 days in a glass tube (this to speed up the phase separation in the emulsion), where a waxy layer is formed adhered to the walls of the tube.

On the other hand, in the case of composition PRO-176 (FIG. 5B), when this test is performed, the layer appears less intense, maintaining a more homogeneous appearance to the naked eye.

On the other hand, a Tolerance analysis was performed using a control solution (NaCl), the composition of the present invention and the commercial product. This to detect the behavior of the contact lenses during the test. Each of the attributes analyzed were plotted and compared with the established limits.

Lens Diameter Type I diopter 1.0

Number of cases: 180

Dependent variable: diameter (mm)

Limits: upper 14.7; middle 14.5; bottom 14.3

Use time 30 days

Figure 6:
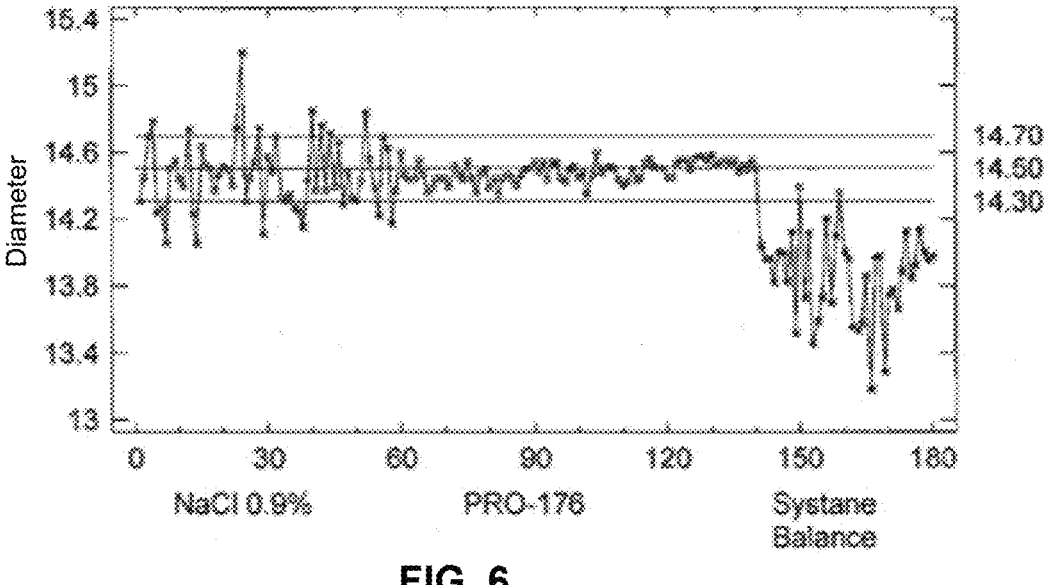
FIG. 6 shows a tolerance graph for the diameter present in Type I contact lenses (Monthly replacement soft contact lens, consisting of 67% Polymer (Lotraficon B) and 33% water) diopter 1.0.

FIG. 6 shows contact lenses with out-of-spec diameters. Both the contact lenses submitted with the control solution (NaCl 0.9%) and the commercial product Systane Balance®. However, the contact lenses subjected to PRO-176 remained within the established specifications.

Lens thickness Type I diopter 1.0

Number of cases: 180

Dependent variable: thickness (mm)

Limits: upper 0.19; center 0.17; lower 0.15

Use time 30 days

Figure 7:
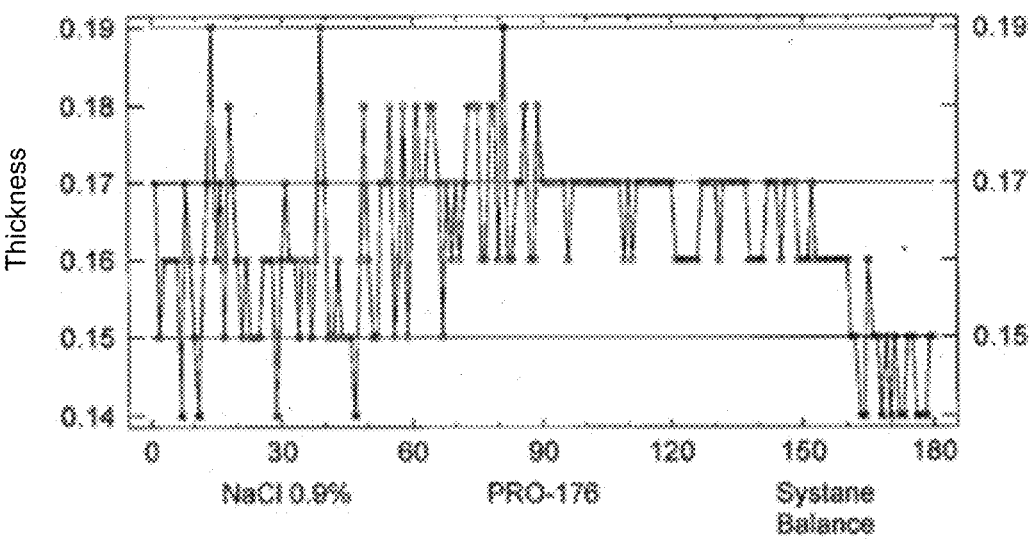
FIG. 7 shows a tolerance graph for the thickness present in Type I contact lenses, diopter 1.0.

FIG. 7 shows contact lenses with out-of-spec thicknesses. Both in the contact lenses submitted with the control solution of NaCl 0.9% and the commercial product Systane Balance®. However, the contact lenses submitted with the PRO-176 remained within the established specifications.

Lens Diameter Type I diopter 6.0

Number of cases: 180

Dependent variable: Diameter (mm)

Limits: upper 14.7; middle 14.5; bottom 14.3

Use time 30 days

Figure 8:
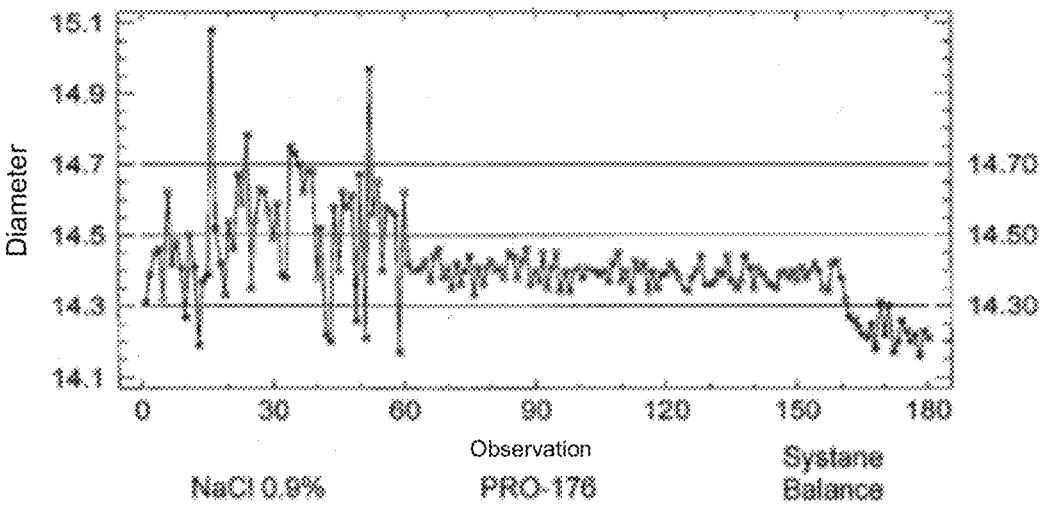
FIG. 8 shows a tolerance graph for the diameter present in Type I contact lenses, diopter 6.0.

FIG. 8 shows diameter data of contact lenses tested with the 0.9% NaCl control solution and with the commercial product Systane Balance®, which show out-of-spec values. However, the diameter present in the contact lenses submitted with PRO-176 remained within the established specifications.

UV light transmittance Lens Type IV diopter 6.0

Number of cases: 180

Dependent variable: UV light transmittance (%)

Limits: upper 35; center 30; bottom 25

Use time 30 days

Figure 9:
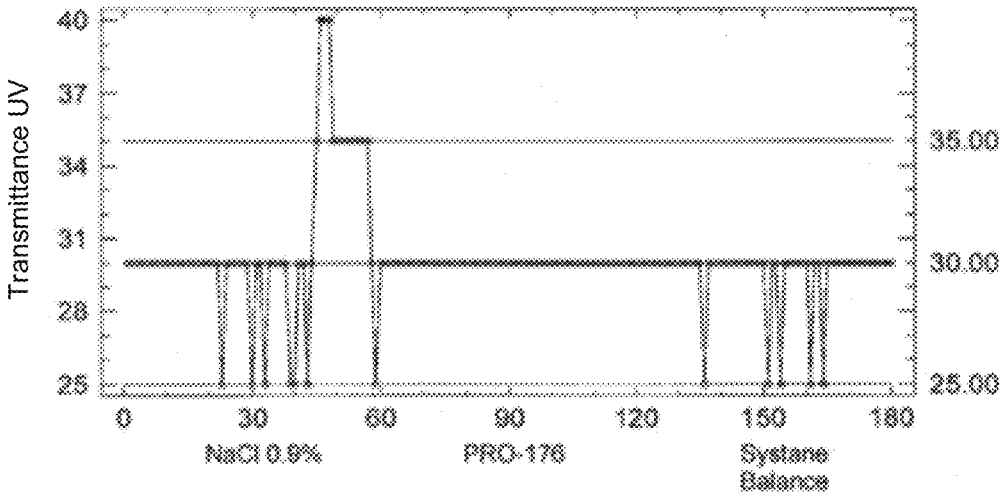
FIG. 9 shows a tolerance graph for the transmittance of UV light present in a Type IV contact lens (Fortnightly replacement soft contact lens, consisting of 42% Polymer (Etafilcon) and 58% water) diopter 6.0.

FIG. 9 shows contact lenses with UV light transmittance values trending towards the upper and lower limits, and out-of-spec data for contact lenses filled with the NaCl 0.9 control solution. In the case of PRO-176 and the commercial product, the data remains within the established specifications, although, in the case of the commercial product, data with a tendency towards the lower limit is shown.

Diopter Lens Tip IV diopter 6.0

Number of cases: 180

Dependent variable: diopters

Limits: upper 6.25; central 6.00; bottom 5.75

Use time 30 days

Figure 10:
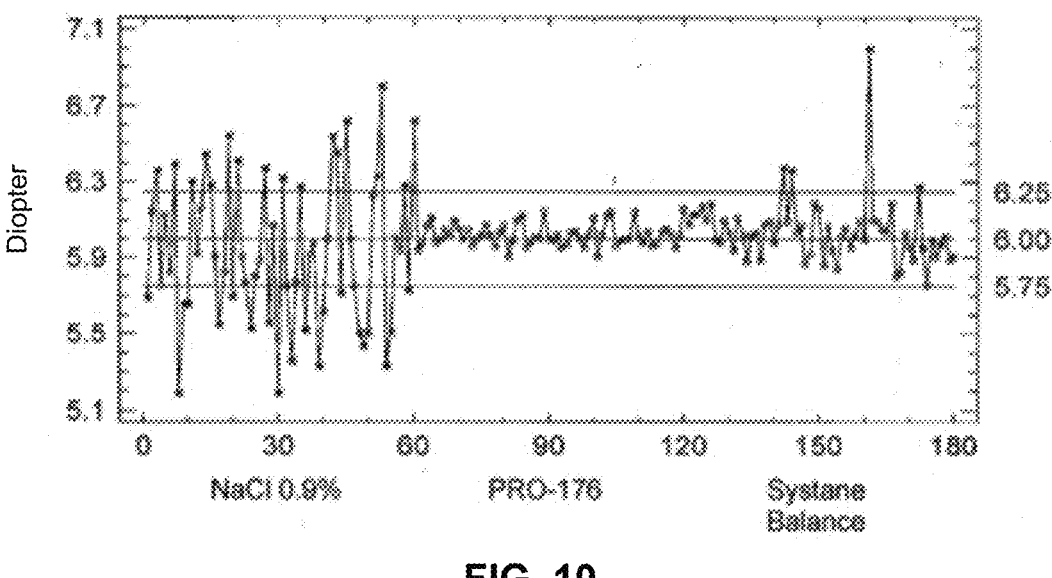
FIG. 10 shows a tolerance graph for diopters present in Type IV contact lenses, diopter 6.0.

FIG. 10 shows contact lenses tested with the 0.9% NaCl control solution and the commercial product showing values out of specifications. In the case of contact lenses treated with PRO-176, no out-of-spec diopters occurred during the study.

Example 3

Polydispersity Index

One of the main properties of an O/W type emulsion is the distribution of the oil particle size, since this property is strongly related to the stability and maintenance of its physicochemical characteristics. This is due to the fact that, when there is a greater number in the oil particle size variability, they flocculate with each other, thereby causing the separation of the lipid phases from the aqueous phase. The manner or form wherein this distribution is established is known as polydispersity.

In such a way that the Polydispersity Index (Pdi) was determined for the composition of the present invention (PRO-176), making a comparison with the commercial product, using a Zetasizer Model Nano ZSP equipment. The viscosity of the samples at a temperature of 25° C. was considered, using the refractive index and dielectric constant of water (1.33/78.50, respectively).

The results are shown below:

| Sample | Batch | Particle size range. (d.nm) Min MAX | Polydispersity index |
|---|---|---|---|
| PRO-176 | 031740 | 1. 32.67-255.0 | Reading 1: 0.200 |
| | | 2. 37.84-220.2 | Reading 2: 0.240 |
| | | 3. 32.67-342.0 | Reading 3: 0.206 |
| | | | Average: 0.215 |
| Systane Balance ® | 263865F | 1. 20.21-531.2 | Reading 1: 0.254 |
| | | 2. 37.84-458.7 | Reading 2: 0.250 |
| | | 3. 43.82-396.1 | Reading 3: 0.239 |
| | | | Average: 0.247 |

According to the results described in the previous Table, it is observed that PRO-176 has a lower polydispersity index (0.215 Pdi), and an average particle size (83.03 d.nm) compared to the commercial product. (0.247 Pdi and 110.63 d.nm). Considering this product with a less homogeneous population of particle sizes than that presented by PRO-176 (Propylene Glycol 0.6%). This is due to the differences between both formulations regarding the amount and type of dispersed oil, as well as the surfactants and dispersing agents used in each formula.

Many modifications and other embodiments of the invention will occur to one skilled in the art to which the invention pertains, having the benefit of the teachings presented in the foregoing descriptions and associated figures. Therefore, it is to be understood that the invention is not to be limited to the specific embodiments disclosed, but modifications and other embodiments are intended to be included within the scope of the appended claims. Although specific terms are used herein, they are used only in a generic and descriptive sense and not for purposes of limitation.

The invention claimed is:

1. An ophthalmic pharmaceutical composition in the form of an oil-in-water (O/W) emulsion comprising:

a) an organic polyol compound;

b) a fragmented polymer, wherein the fragmented polymer comprises monomers;

c) at least one synthetic phospholipid of a phosphatidyl-choline type; and d) at least one pharmaceutically acceptable excipient.

2. The composition according to claim 1, wherein the organic polyol compound is selected from the group consisting of propylene glycol, polyethylene glycol 300 and sorbitol.

3. The composition according to claim 1, wherein the fragmented polymer is selected from the group consisting of guar gum, gellan gum, hydroxypropylmethylcellulose, sodium hyaluronate, hydroxyethylcellulose, methylcellulose, polyvinylpyrrolidone and polyvinyl alcohol.

4. The composition according to claim 1, further comprising castor oil and the phospholipid is selected from the group consisting of DPPC (1,2-dipalmitol-sn-glycero-3-phosphocholine), DSPC (1,2-distearol-sn-glycero-3-phosphocholine, DOPC (1,2-Dioleol-sn-glycero-3-phosphocholine), DEPC (1,2-dierucil-sn-glycero-3-phosphocholine), and DMPC (1,2-dimyristoyl-sn-glycero-3-phosphocholine).

5. The composition according to claim 1, wherein the pharmaceutically acceptable excipients are selected from the group consisting of surfactants, boric acid, sodium borate decahydrate, disodium edetate dihydrate, glycerin, and mixtures thereof.

6. The composition according to claim 1, wherein the organic polyol compound is propylene glycol.

7. The composition according to claim 1, wherein the fragmented polymer is sodium hyaluronate.

8. The composition according to claim 1, wherein the phospholipid is 1,2-dimyristoyl-sn-glycero-3-phosphocholine (DMPC).

9. The composition according to claim 4, wherein:

the propylene glycol is in a ratio between 0.1 to 0.6% w/v;

the fragmented polymer is in a proportion of 0.1 to 0.5% w/v;

the phospholipid is DMPC in a proportion between 0.001 to 0.01% w/v; and the castor oil is in a proportion of between 1.0 to 5.0% w/v.

10. The composition according to claim 7, wherein the sodium hyaluronate is fragmented in the form of monomers dispersed in the composition.

11. The composition according to claim 1, wherein the phospholipid forms micelles and the particle size distribution in the micelles is between 30 to 260 nm, optionally between 32 to 255 nm or between 82.5 to 92.5 nm.

12. The composition of claim 1, wherein the composition is adapted to: maintain the diameter of a soft contact lens within about 1.5 to about 2% of the initial diameter of the soft contact lens; maintain the thickness of the soft contact lens within 10% of the initial thickness of the soft contact lens; maintain the UV light transmittance value of the soft contact lens within about +/−5.0% of the initial UV light transmittance values of the soft contact lens; and maintain the diopters of the soft contact lens within about +/−25% of the initial diopters of the soft contact lens.

13. A method for the manufacture of the ophthalmic pharmaceutical composition of claim 1, the method comprising:

(a) adding water to a tank at a temperature from about 20 to about 30° C.;

(b) adding to (a): 1,2-dimyristoyl-sn-glycero-3-phosphocholine (DMPC), boric acid, sodium borate decahydrate, disodium edetate dihydrate, glycerin, propylene glycol, sodium hyaluronate and castor oil and further adding at least one surfactant to produce an oily-aqueous preparation, wherein the water constitutes about 60% to about 65% of the volume of the composition and the water is agitated during the step of adding (b);

(c) emulsifying the oily-aqueous preparation of (b) to produce an emulsion;

(d) sterilizing the emulsion of (c) by filtration to produce a sterilized filtered emulsion; and (e) homogenizing and emulsifying the sterilized filtered emulsion of (d) to produce the ophthalmic pharmaceutical composition.

14. The method of claim 13, wherein the tank of (a) is a stainless-steel tank and/or the water of (a) is injectable grade water.

15. The method of claim 13, wherein the agitation of the water in (b) is constant, and/or the emulsifying of (c) is a mechanical emulsification process, optionally the agitation is in a range of 78 rpm to about 840 rpm.

16. The method of claim 13, wherein: the filtration of (d) comprises filtering through sterilizing membranes, optionally wherein the sterilizing membranes have a pore size of about 0.2 μm, the homogenizing of (e) comprises about a 60-minute homogenization process, and/or the emulsifying of (e) comprises a three-cycle mechanical emulsification process in a pressure range of about 10,000 psi to about 30,000 psi.

17. A container comprising the ophthalmic pharmaceutical composition according to claim 1.

18. A pharmaceutical system comprising:

(a) a low-density polyethylene container with an assembled high-density polyethylene closure-device, wherein the low-density polyethylene container comprises a system of silicone and low-density polyethylene valves;

(b) the ophthalmic pharmaceutical composition of claim 1; and (c) a buffer solution based on borates in a proportion not greater than 0.1%.

19. The pharmaceutical system according to claim 18, wherein the system is adapted for the conservation and administration of the composition of claim 1, at a pH of between 6.5 to 7.5 and an osmolality of 200 to 400 mOsmol/kg.

20. A method for treating and/or relieving dry eye and/or non-bacterial conjunctivitis in a subject in need thereof, the method comprising administering the ophthalmic pharmaceutical composition of claim 1 to the subject.

* * * * *